United States Patent
Schraeml et al.

(10) Patent No.: US 12,158,466 B2
(45) Date of Patent: Dec. 3, 2024

(54) METHOD FOR DETERMINING THE TOTAL AMOUNT AND/OR CONCENTRATION OF AN ANALYTE IN THE PRESENCE OF A BINDING MOLECULE AS WELL AS KITS, COMPOSITIONS AND USES RELATING THERETO

(71) Applicant: Roche Diagnostics Operations, Inc., Indianapolis, IN (US)

(72) Inventors: Michael Schraeml, Penzberg (DE); Markus Roessler, Germering (DE); Michael Gerg, Munich (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 1035 days.

(21) Appl. No.: 16/734,884

(22) Filed: Jan. 6, 2020

(65) Prior Publication Data
US 2020/0141930 A1    May 7, 2020

Related U.S. Application Data

(60) Division of application No. 15/146,226, filed on May 4, 2016, now Pat. No. 10,564,151, which is a (Continued)

(30) Foreign Application Priority Data

Nov. 5, 2013   (EP) ..................................... 13005218
Jun. 11, 2014  (EP) ..................................... 14002015

(51) Int. Cl.
G01N 33/543   (2006.01)
G01N 33/53    (2006.01)

(52) U.S. Cl.
CPC ........... *G01N 33/543* (2013.01); *G01N 33/53* (2013.01)

(58) Field of Classification Search
CPC ............................. G01N 33/543; G01N 33/53
See application file for complete search history.

(56) References Cited

U.S. PATENT DOCUMENTS 4,208,479 A * 6/1980 Zuk ...................... C07J 41/0016
                                                          436/826
5,312,730 A    5/1994 Piran et al.
(Continued)

FOREIGN PATENT DOCUMENTS

CN    101186651 A    5/2008
CN    101541835 A    9/2009
(Continued)

OTHER PUBLICATIONS

Altamirano-Bustamante et al. "Direct time-resolved fluorescence immunoassay for serum oestradiol based on the idiotypic anti-idiotypic approach" J. Immunol. Methods 1991 138:95-101 (Year: 1991).*

(Continued)

*Primary Examiner* — Changhwa J Cheu
(74) *Attorney, Agent, or Firm* — Taft Stettinius & Hollister LLP

(57) ABSTRACT

The present invention relates to a method for determining the total amount and/or concentration of an analyte in the presence of a binding molecule as well as kits, compositions and uses relating thereto.

4 Claims, 3 Drawing Sheets

Related U.S. Application Data continuation of application No. PCT/EP2014/073523, filed on Nov. 3, 2014.

(56) References Cited

U.S. PATENT DOCUMENTS

| | | | | |
|---|---|---|---|---|
| 6,040,134 | A * | 3/2000 | Madsen | C07K 14/4713 436/63 |
| 9,671,394 | B2 | 6/2017 | Stubenrauch et al. | |
| 9,880,176 | B2 * | 1/2018 | Jaga | G01N 33/6854 |
| 2008/0206782 | A1 * | 8/2008 | Golden | G01N 33/686 435/7.1 |
| 2008/0268459 | A1 * | 10/2008 | Liu | C07K 16/2896 435/7.1 |
| 2008/0318339 | A1 * | 12/2008 | Vossenaar | G01N 33/686 422/68.1 |
| 2009/0246795 | A1 | 10/2009 | Hayashi et al. | |
| 2015/0050273 | A1 * | 2/2015 | Harding | A61P 1/00 435/69.6 |
| 2015/0198608 | A1 | 7/2015 | Stubenrauch et al. | |

FOREIGN PATENT DOCUMENTS

| | | | |
|---|---|---|---|
| EP | 1139101 | A2 | 10/2001 |
| WO | 1993/022675 | A1 | 11/1993 |
| WO | 2005/108989 | A2 | 11/2005 |
| WO | 2007/072922 | A1 | 6/2007 |
| WO | 2009/032128 | A1 | 3/2009 |
| WO | WO-2013092611 | A2 * | 6/2013 ............ G01N 33/53 |
| WO | 2013/113663 | A1 | 8/2013 |

OTHER PUBLICATIONS

Kobayashi et al. "Immunoenzymometric assay for a small molecule, 11-deoxycortisol, with attomole range sensitivity employing an scFv-enzyme fusion protein and anti-idiotype antibodies" Anal. Chem. 2006 78:2244-2253. (Year: 2006).*

Kohen et al. "Generation of an anti-idiotypic antibodies as a surrogate ligand for sulfamethazine in immunoassay procedures" Food and Agricultural Immunology 2000 12:193-201 (Year: 2000).*

Ponomarenko et al. "Anti-idiotypic antibody mimics proteolytic function of parent antigen" Biochemistry 2007 46: 14598-14609 (Year: 2007).*

Schouwenburg (II) et al. "Adalimumab elicits a restricted anti-idiotypic antibody response in autoimmune patients resulting in functional neutralisation" Ann. Rheum Dis 2013 72:104-019 (Year: 2013).*

Department of Antibody Development, Martinsried: Pharmacokinetics, immunogenicity and bioactivity of the therapeutic antibody catumaxomab intraperitoneally administered to cancer patients, Catumaxomab Development in Symposium Abstract, 2010, 2 pp., Springer, New York.

International Search Report dated Dec. 3, 2014, in Application No. PCT/EP2014/073523, 3 pages.

Lee, Jean W. et al., Bioanalytical Approaches to Quantify "Total" and "Free" Therapeutic Antibodies and Their Targets: Technical Challenges and PK/PD Applications Over the Course of Drug Development, The AAPS Journal, 2011, pp. 99-110, vol. 13, No. 1.

Malmqvist, Magnus, Surface plasmon resonance for detection and measurement of antibody-antigen affinity and kinetics, Current Opinion in Immunology, 1993, pp. 282-286, vol. 5.

Moroney, John W. et al., Aflibercept in epithelial ovarian carcinoma, Future Oncology, 2009, pp. 591-600, vol. 5, No. 5.

Pan, Ying et al., Anti-idiotypic antibodies: biological function and structural studies, FASEB Journal, 1995, pp. 43-49, vol. 9.

Patton, Aaron et al., An acid dissociation bridging ELISA for detection of antibodies directed against therapeutic proteins in the presence of antigen, Journal of Immunological Methods, 2005, pp. 189-195, vol. 304.

Salimi-Moosavi, Hossein et al., Novel approaches using alkaline or acid/guanidine treatment to eliminate therapeutic antibody interference in the measurement of total target ligand, Journal of Pharmaceutical and Biomedical Analysis, 2010, pp. 1128-1133, vol. 51, No. 5.

Schräml, Michael and Biehl, Matthias, Kinetic Screening in the Antibody Development Process, Methods in Molecular Biology, 2012, pp. 171-181, vol. 901, Ch. 11.

Sege, Karin and Peterson, Per A., Use of anti-idiotypic antibodies as cell-surface receptor probes, Proceedings of the National Academy of Sciences USA, 1978, pp. 2443-2447, vol. 75, No. 5.

Suzuki, Yoshihito et al., Preparation and Application of Anti-idiotypic Antibody against Anti-gibberellin A4 Antibody, Bioscience Biotechnology and Biochemistry, 1999, pp. 648-654, vol. 63, No. 4.

Van Schouwenburg, et al., A novel method for the detection of antibodies to adalimumab in the presence of drug reveals "hidden" immunogenicity in rheumatoid arthritis patients, J. Immuno. Meth., 2010, pp. 82-88, vol. 362.

Verch, Thorsten et al., Pharmacokinetic immunoassay methods in the presence of soluble target, Journal of Immunological Methods, 2010, pp. 75-81, vol. 361.

* cited by examiner

METHOD FOR DETERMINING THE TOTAL AMOUNT AND/OR CONCENTRATION OF AN ANALYTE IN THE PRESENCE OF A BINDING MOLECULE AS WELL AS KITS, COMPOSITIONS AND USES RELATING THERETO

CROSS-REFERENCE TO RELATED APPLICATIONS

This application is a divisional of U.S. application Ser. No. 15/146,226 filed May 4, 2016 (now allowed), which is a continuation of International Patent Application No. PCT/EP2014/073523 filed Nov. 3, 2014, and claims priority to EP Patent Application No. 13005218.6 filed Nov. 5, 2013, and EP Patent Application No. 14002015.7 filed Jun. 11, 2014, the disclosures of which are hereby incorporated by reference in their entirety.

BACKGROUND OF THE DISCLOSURE

In the context of many applications employing binding molecules, e.g. for therapeutically active antibodies directed to a target in an animal or human, there is a need for methods which enable the determination of such target in the presence of the binding molecule, without the requirement to remove the binding molecule prior to determining the amount or concentration of the target. In particular for e.g. therapeutically active antibodies or therapeutically active receptors or receptor fragments, there is a need for in vitro methods which allow the determination in bodily samples of the total amount or concentration of the target against which the therapeutically active antibody or therapeutically active receptor or receptor fragments is directed, without removing from the sample the therapeutically active antibody or therapeutically active receptor or fusion protein. The total amount thereby comprises both free, unbound target, and target bound to the therapeutically active antibody or therapeutically active receptor or receptor fragments.

BRIEF SUMMARY OF THE DISCLOSURE

The present invention relates to a method for determining the total amount and/or concentration of an analyte in the presence of a binding molecule as well as kits, compositions and uses relating thereto. Among the inventions many uses are improvements for in vitro methods which allow the determination in bodily samples of the total amount or concentration of the target against which the therapeutically active antibody or therapeutically active receptor or receptor fragments is directed, without removing from the sample the therapeutically active antibody or therapeutically active receptor or fusion protein.

DETAILED DESCRIPTION OF THE DISCLOSURE

Figure 1A:
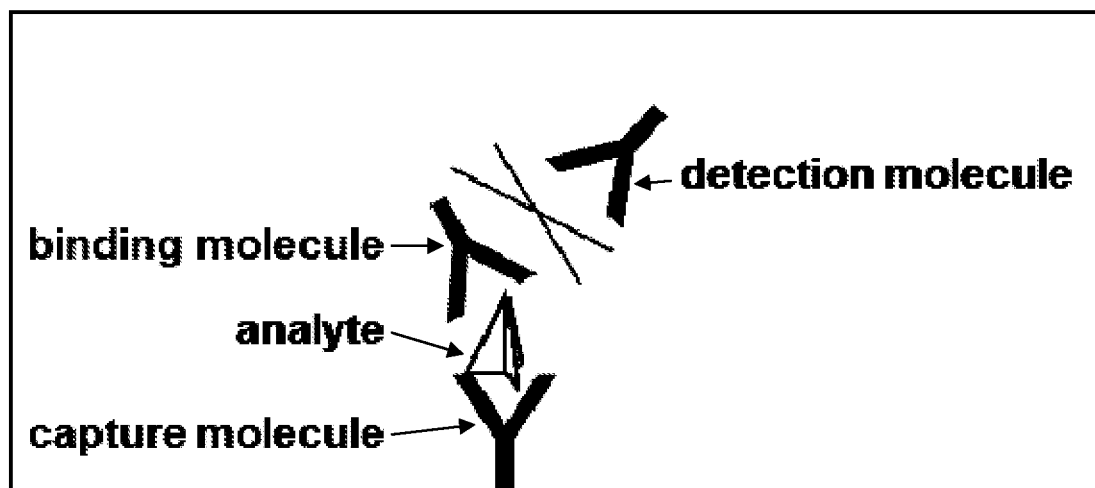
FIG. 1A: represents a schematic illustration of a preferred method of the invention. This figure illustrates the situation, wherein the binding molecule binds to the analyte, which is immobilized via the capture molecule. The detection molecule cannot bind to the analyte.

The present invention makes available such methods and kits which can be used in the methods of the invention:

In one embodiment the present invention relates to an in vitro method for determining the total amount and/or concentration of an analyte in the presence of a binding molecule capable of binding with its binding site to the analyte, the method comprising the steps:

(i) contacting a sample comprising the analyte and the binding molecule with
  a trapping molecule directed against the binding site of the binding molecule and
  a detection molecule capable of forming a complex with the analyte, and
(ii) detecting the detection molecule-analyte complex, thereby determining the total amount and/or concentration of the analyte,
  wherein the detection molecule is different from the binding molecule, and
  wherein the analyte is different from the trapping molecule, and
  wherein the detection molecule is only capable of forming a complex with the analyte when the analyte is not bound by the binding molecule.

As a first step, a sample comprising the analyte and the binding molecule is contacted with a trapping molecule directed against the binding site of the binding molecule and a detection molecule capable of forming a complex with the analyte.

The analyte to be measured may be any chemical compound. Typically, such analyte may be an analyte present in a biological sample, in particular a bodily fluid from a human or animal. In particular, the analyte may be a biomarker, peptide and/or protein.

The sample which comprises the analyte may be a liquid, gel or liquefiable composition, preferably a liquid. Such liquid may be a solution, suspension or emulsion. In particular, the sample is a biological sample, in particular a bodily sample obtained from a human or animal, or mixtures thereof. Such bodily sample may be used directly after retrieval from a subject, or may be stored under adequate conditions, e.g. by freezing, in order to perform the method of the invention at a intended point of time. In particular, samples from various subjects and/or different time points may be measured in order to compare subjects or to monitor a therapy. The retrieval of a bodily sample may be performed by a skilled person depending on the sample. In a preferred embodiment, the bodily sample is blood or blood serum. In such case, blood is taken from a subject. Blood serum may be obtained from blood by methods known in the art. Similarly, other bodily samples may be obtained by e.g. collecting urine, or by taking a biopsy, and by further treatment of the sample, if necessary.

As described above, the sample comprises the analyte and a binding molecule capable of binding with its binding site to the analyte. Such binding molecule may be any type of molecule, which is capable of binding to the analyte. Such binding is preferably reversible and non-covalent. Preferably, such binding molecule is or comprises a protein or peptide. More preferably, the binding molecule comprises an antibody, a functionally active part of an antibody, a receptor or a receptor fragment, in particular a therapeutically and/or diagnostically active antibody or therapeutically and/or diagnostically active functionally active part of an antibody or therapeutically and/or diagnostically active receptor or therapeutically and/or diagnostically active receptor fragment. Thus, the binding molecule is in a preferred embodiment a therapeutic and/or diagnostic agent. As an example, the binding molecule is a therapeutic agent which was administered to a human subject in need thereof. In the body of the subject, the binding molecule binds the analyte, which represents in such scenario the target of the therapeutic agent. Upon retrieval of the sample from the subject, the sample will typically comprise both analyte and therapeutic agent. As the therapeutic agent can bind to the analyte, some or all of the analyte will be bound to the therapeutic agent.

The binding molecule is capable of binding with its binding site to the analyte. A binding site is a region on a molecule, in particular protein, DNA, or RNA, more preferably protein, to which at least one specific other molecule can bind non-covalently and reversibly. In case of antibodies recognizing an antigen as preferred pair of binding molecule and antigen, the binding site is often referred to as antigen binding site, and the site bound by the binding site is often referred to as epitope. Binding sites exist on antibodies as specifically coded regions that bind antigens based upon their structure, as explained below in more detail.

As a first step in the method of the invention, a sample comprising the analyte and the binding molecule is contacted with a trapping molecule directed against the binding site of the binding molecule and a detection molecule capable of forming a complex with the analyte. The trapping molecule may be any chemical compound, preferably it is a protein, more preferably an antibody or functionally active part of an antibody or a receptor or receptor fragment. The trapping molecule is directed against the binding site of the binding molecule, which means that the trapping molecule is capable of binding to said binding site of the binding molecule either covalently or non-covalently, preferably non-covalently. In an also preferred embodiment, the trapping molecule is an antibody or functionally active part. In a further preferred embodiment, the trapping molecule is an anti-idiotype antibody. An anti-idiotype antibody or functionally active part thereof is an antibody or functionally active part thereof directed against the antigen-specific part of an antibody and thus recognizes the binding site of another antibody. In such embodiment, also the binding molecule is an antibody or functionally active part thereof.

The detection molecule capable of forming a complex with the analyte may be any kind of chemical compound, preferably it is a protein, DNA or RNA, more preferably a protein, even more preferably an antibody or functionally active part thereof, with the prerequisite that the detection molecule is different from the binding molecule. In an also preferred embodiment, the detection molecule is an antibody or functionally active part. The detection molecule carries means for detectable labeling with a detectable label, particularly means for direct or indirect detection. Such means and labels are described below in more detail. That the detection molecule is different from the binding molecule is to be understood that both molecules are different molecules even ignoring means for detectable labeling, more preferably their binding sites capable of binding the analyte are different. In case of the binding molecule and the detection molecule both comprising or being an antibody or functionally active part thereof, the antigen binding sites are preferably different, more preferably 1, 2, 3, 4, 5, or 6 of the corresponding CDR sequences (HCDR 1, 2, 3 and LCDR1, 2, 3) are different.

The detection molecule is capable of forming a complex with the analyte. This means that the detection molecule can bind to the analyte covalently or non-covalently. In case of non-covalent binding, as in case of antibody-antigen binding, the detection molecule preferably exhibits a sufficiently high affinity to this analyte for complex formation. Therefore, in a further preferred embodiment, the affinity of the detection molecule for binding to the analyte is at least $10^8$ $(mol/l)^{-1}$, more preferably $10^9$ $(mol/l)^{-1}$, even more preferably of at least $10^{10}$ $(mol/l)^{-1}$. The affinity can be determined by methods known in the art, in particular by surface plasmon resonance measurements, in particular employing the BiaCore® system. Moreover, the detection molecule is only capable of forming a complex with the analyte when the analyte is not bound by the binding molecule. As illustrated in FIG. 1B, such detection molecule will only form a complex with the analyte if the binding molecule is released from the analyte by the binding of the binding molecule to the trapping molecule.

According to the invention, a sample comprising the analyte and the binding molecule is contacted with a trapping molecule directed against the binding site of the binding molecule and a detection molecule capable of forming a complex with the analyte. The contacting may be performed by methods known in the art. In particular, a sample may be provided in a suitable container, and the trapping molecule and detection molecule may be added separately or together, e.g. by pipetting solutions comprising the trapping molecule and/or the detection molecule; however the sequence of contacting the components is not decisive. Suitable conditions include appropriate temperature and solution to avoid e.g. undesired chemical modifications of compounds, loss of respective binding capability, denaturation of proteins involved or to maintain viable cells, if present.

That the trapping molecule is different from the analyte is to be understood that both molecules are different molecules. In a preferred embodiment, their binding sites capable of binding the binding molecule are different. In case of the trapping molecule and the analyte both comprising or being an antibody or functionally active part thereof, the antigen binding sites are preferably different, more preferably 1, 2, 3, 4, 5, or 6 of the corresponding CDR sequences (HCDR 1, 2, 3 and LCDR1, 2, 3) are different.

Suitable conditions for performing the method of the invention will depend on the particular assay design and components chosen, and the skilled person will be able to select the same based on his general knowledge. Incubation steps can vary from about 5 seconds to several hours, preferably from about 5 minutes to about 24 hours. However, the incubation time will depend upon the assay format, label, volume of solution, concentrations and the like. Usually, the assays will be carried out at ambient temperature, although they can be conducted over a range of temperatures, such as 10° C. to 95° C. or 15° C. to 40° C. Also, the container used will depend on the assay format, label, volume of solution, concentrations and the like.

The method of the invention allows determining the total amount and/or concentration of such analyte. In the sample, both the analyte and the binding molecule are present. As binding molecules often occupy suitable binding sites on an analyte and/or hinder binding of a detection molecule due to sterical reasons, the determination of the total amount of analyte in the sample is difficult. The total amount of analyte means the number of all analyte molecules in a given sample, both analytes which are free, unbound vis-à-vis the binding molecule, and analyte molecules which are bound to the binding molecule. In an analogous manner, the total concentration of such analyte in a given sample can be determined, meaning the concentration of all analyte molecules in a given sample, both analytes which are free, unbound vis-à-vis the binding molecule, and analyte molecules which are bound to the binding molecule. The concentration is typically given as molar concentration or (w/v) concentration.

As a second step of the method of the invention, the detection molecule-analyte complex is detected. As explained above, such complex may be covalent or non-covalent. By performing the first step of the invention, the detection molecule may now form a complex with all analyte molecules present in the sample, as the binding molecules are trapped by the trapping molecule, as illustrated in FIG. 1B. Detection of the detection molecule-analyte complex therefore allows determining the amount and/or concentration of the total amount of analyte molecules, irrespective of whether they were initially bound to a binding molecule or not. The detection of the complex may be performed in various ways depending on the assay format and/or label explained in more detail below. Preferred assays are non-competitive assays, particularly sandwich assays.

Thus, in a preferred embodiment of the present invention, detecting the detection molecule-analyte complex is performed in a non-competitive assay, particularly in a sandwich assay, especially wherein the sandwich assay employs a capture molecule capable of binding to the analyte, and wherein
    the capture molecule carries means for immobilization, and
    the detection molecule and the capture molecule bind to different, non-overlapping epitopes on the analyte.

Figure 1B:
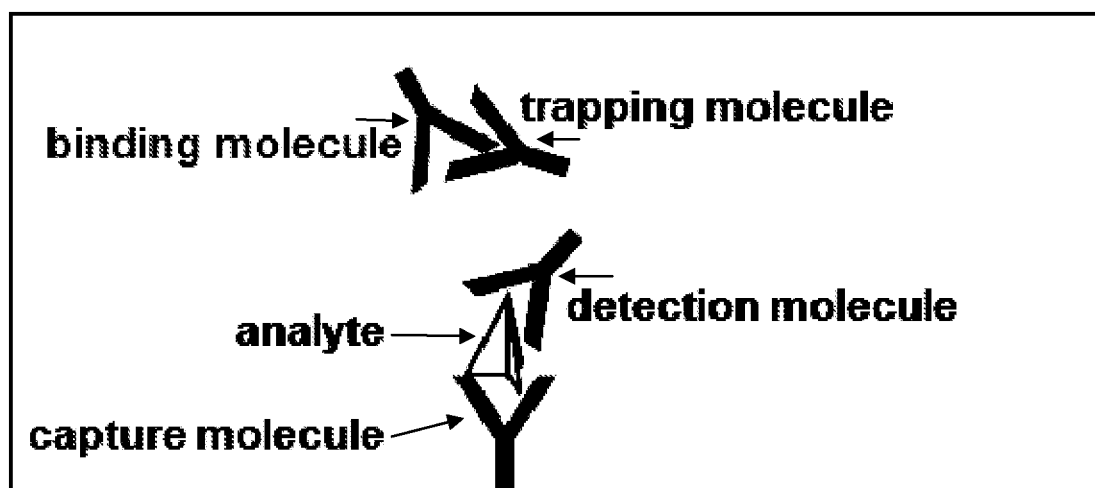
FIG. 1B: represents a schematic illustration of a preferred method of the invention. In this situation the trapping molecule binds to the binding molecule, which is thereby released from the analyte. The detection molecule can now bind to the immobilized analyte. This allows the determination of essentially the total amount or concentration of the analyte in question, although the binding molecule is present in the sample.

The invention according such preferred embodiment is illustrated in FIG. 1. In this embodiment, the analyte is captured to a support via the capture molecule, and is thereby immobilized. In the sample, at least some of the analyte molecules are bound by the binding molecule. In this situation, the detection molecule cannot bind to the analyte bound by the binding molecule (FIG. 1A), as the detection molecule is only capable of forming a complex with the analyte when the analyte is not bound by the binding molecule. Therefore, bound analyte cannot be detected in this situation. Upon addition of the trapping molecule, the binding molecule is released from the analyte, and the detection analyte can bind to the analyte molecule (FIG. 1B). In this situation, the detection molecule can bind to essentially all analyte molecules present in the sample, and the total amount or concentration of analyte can be determined.

In such preferred embodiment, a capture molecule carries means for immobilization and can be used for immobilization. The means for immobilization may allow binding to a support, preferably solid support, covalently or non-covalently.

The term "solid support" refers to a material in the solid-phase that interacts with reagents in the liquid phase by heterogeneous reactions. The use of solid supports is well known in the fields of chemistry, biochemistry, pharmacy and molecular biology. Many types of solid supports have been developed depending on the technical problem to be solved. Any of these may be used in the context of the present invention. For example, the solid support used in the methods of the present invention may include components of silica, cellulose acetate, nitrocellulose, nylon, polyester, polyethersulfone, polyolefin, or polyvinylidene fluoride, or combinations thereof. Further suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

Common resin supports used e.g. in combinatorial or protein chemistry include polystyrene resin, e.g. cross-linked with divinylbenzene; hydroxymethylpolystyrene; aminomethylpolystyrene; TentaGel resin (TG) and ArgoGel (AG): polystyrene/DVB-poly(ethylene glycol) graft copolymers (PS-PEG)—Bayer; Crowns/Pins (CP) (radiation-grafted polyethylene/polypropylene support); Kieselguhr/polyacrylamide-based resins (KPA); Controlled-pore glass; PEGA—poly(ethylene glycol)/dimethylacrylamide copolymer.

Immobilization to a solid support may be accomplished using solid supports that have been modified or activated to include functional groups that permit the covalent coupling of the entity or support to the capture molecule, e.g. a protein. Typically, aliphatic linker arms are employed. The capture molecules, particularly proteins, can also be noncovalently attached to a surface, through, for example, ionic or hydrophobic mechanisms, and are detached by the releaser inhibiting these mechanisms locally. Additionally, covalent attachment of an capture molecule, e.g. a protein, to a surface, e.g. a glass or metal oxide surface, can be accomplished by first activating the surface with an amino silane. Capture molecules derivatized with amine-reactive functional groups can then attach to the surface. Supports, in particular solid supports can be derivatized with proteins such as enzymes, peptides, oligonucleotides and polynucleotides by covalent or non-covalent bonding through one or more attachment sites, thereby binding the same acid to the solid support.

The (solid) support may be contained in a vessel, wherein the vessel is a tube, such as a centrifuge tube or spin tube, syringes, cartridge, chamber, multiple-well plate, or test tube, or combinations thereof. The (solid) support may be pre-treated or functionalized in order to allow linker-mediated binding of the capture molecules. In one embodiment, the solid support may be fibrous or particulate usually allowing for appropriate contacting. The size of the (solid) support suitable for use in the method of this invention may vary according to method chosen. The capture molecules may be bound to one (solid) support only (e.g. one vessel or multi-well plate) or may be bound to a multitude of (solid) supports (e.g. beads). The shape of the (solid) support suitable for use in the methods of this invention may be, for example, a sheet, a precut disk, cylinder, single fiber, or a solid support composed of particulates. In one embodiment, the (solid) support may be fibrous or particulate to allow optimal contacting. The size of the (solid) support may vary and may be chosen depending on the method to be carried out.

In some embodiments, the solid phase is a test strip, a chip, in particular a microarray or nanoarray chip, a microtiter-plate or a microparticle.

It is advantageous if essentially complete release of the analyte from the binding molecule is achieved upon addition of the trapping molecule, as this facilitates the correct determination of the total amount of analyte in the sample, as illustrated in FIG. 1B. Therefore, in a preferred embodiment of the present invention, the trapping molecule facilitates the essentially complete release of the analyte from the binding molecule.

"Essentially complete release" according to the present invention is understood as that less than 10%, preferably less than 5%, more preferably less than 1% of the analyte molecules are bound to a binding molecule in the sample after step (i) of the invention.

According to the present invention, K(trap) is the affinity of the trapping molecule for the binding molecule, and K(binding molecule) is affinity of the binding molecule for the analyte.

"Affinity" defines the strength of interaction between the two species, and is preferably determined via surface plasmon resonance, in particular using the BiaCore® system. In case of antibodies or antibody fragments, the affinity is determined as $K_D$ value preferably determined via surface plasmon resonance, in particular using the BiaCore® system. The determination of the affinity can be performed as described in "Surface plasmon resonance for detection and measurement of antibody-antigen affinity and kinetics", Current Opinion in Immunology, Volume 5, Issue 2, 1993, Pages 282-286.

Moreover, according to the invention, Conc(trap) and Conc(binding molecule) are the molar concentrations of the trapping molecule and the binding molecule, respectively, in step i) of the method of the invention above.

Moreover, according to the invention, MR(trap) is the binding valence of the trapping molecule for binding to the binding molecule and MR(binding molecule) is binding valence of the binding molecule for binding to the analyte.

"Binding valence" according to the present invention is understood as the experimentally determined number of binding sites for a given pair of binding partners. In case of antibodies or functionally active parts thereof, the theoretical binding valence is typically 1 or 2, but experimentally determined binding valences may be non-integer values (e.g. 1.4) due to sterical effects. In case of anti-idiotype antibodies as preferred trapping molecules, the theoretical binding valence is typically 1. Again, the experimentally determined binding valence may be a non-integer value (e.g. 0.9) due to sterical effects. The determination of the binding valence can be performed as described in Schraeml M. et al. (2012) Methods in Molecular Biology Vol. 901, 171-181.

In order to achieve essentially complete release of the binding molecule from the analyte, it is advantageous if the affinity of the trapping molecule for the binding molecule is at least 3-fold higher than the affinity of the binding molecule for the analyte. Therefore, in a further preferred embodiment, K(trap)/K(binding molecule) is at least 3, preferably 5, more preferably at least 10.

In order to achieve essentially complete release of the binding molecule from the analyte, it is further advantageous if the concentration of the trapping molecule is at least 3-fold higher than the concentration of the binding molecule. Therefore, in a yet further preferred embodiment, Conc(trap)/Conc(binding molecule) is at least 3, preferably 5, more preferably at least 10, particularly wherein Conc (binding molecule) is in the range of from 1 to 5 µmol/l and/or Conc(trap) is in the range of from 3*(1 to 5) µmol/l.

It is even more advantageous in order to achieve essentially complete release of the binding molecule from the analyte if both the respective affinities and concentrations discussed above are taken into account; in particular it is preferred that the affinity of the trapping molecule for the binding molecule multiplied by the molar concentration of the trapping molecule is at least 3-fold higher than the affinity of the binding molecule for the analyte multiplied by the molar concentration of the binding molecule. Therefore, in an also preferred embodiment, (K(trap)/K(binding molecule))×(Conc(trap)/Conc(binding molecule)) is at least 3, preferably 5, further preferably at least 10.

Another important aspect is the binding valences of the binding molecule and the trapping molecule employed in the method of the invention, in particular in case the binding molecule and/or the trapping molecule are antibodies or functionally active parts thereof. When binding to small analytes, a binding molecule being an antibody typically shows a binding valence of MR=2, whereas for sterical reasons, the trapping molecule being an anti-idiotype antibody typically shows a binding valence of MR=1 and smaller. In this case, the functional molarity quotient is preferably to be considered.

Therefore, in a yet further preferred embodiment, (K(trap)/K(binding molecule))×(Conc(trap)/Conc(binding molecule))×(MR(trap)/MR(binding molecule)) is at least 3, preferably 5, also preferably at least 10.

It is further advantageous for determining the total amount of analyte if the detection molecule, which is intended to bind the analyte, exhibits a sufficiently high affinity to this analyte. Therefore, in a further preferred embodiment, the affinity of the detection molecule for binding to the analyte is at least $10^8$ $(mol/l)^{-1}$, more preferably $10^9$ $(mol/l)^{-1}$, even more preferably of at least $10^{10}$ $(mol/l)^{-1}$.

It is further advantageous for determining the total amount of analyte if the affinity of the trapping molecule for binding to the binding molecule is sufficiently high in order to achieve essentially complete release of the binding molecule from the analyte. Therefore, in a yet further preferred embodiment, the affinity of the trapping molecule for binding to the binding molecule is at least $5×10^9$ $(mol/l)^{-1}$, more preferably of at least $10^{10}$ $(mol/l)^{-1}$.

It is further advantageous if the detection molecule exhibits specificity for the analyte in order to minimize false-positive detection of analyte. Therefore, in a preferred embodiment, the detection molecule binds the analyte specifically, in particular binding of the detection molecule to a target different from the analyte is at most 5% of the binding of the detection molecule to the analyte.

Further, it is advantageous if the trapping molecule exhibits specificity for the binding molecule, in particular in order to minimize loss of the trapping molecule and to maximize binding to the binding molecule. Therefore, preferably, the trapping molecule binds the binding molecule specifically, in particular binding of the trapping molecule to a target different from the binding molecule is at most 5% of the binding of the trapping molecule to the binding molecule.

"Specific" or "specificity" in reference to the binding of one molecule to another molecule, such as the binding of the trapping molecule to the binding molecule, means the recognition, contact, and formation of a stable complex between the identifier and the target object, together with substantially less recognition, contact, or complex formation of the identifier with objects other than the target object (also referred to as other objects). In one aspect, "specific" in reference to the binding of the identifier to the target object means that to the extent the identifier recognizes and forms a complex with the target object, it forms the largest number of the complexes with the target object in comparison to the other objects. In one aspect, this largest number is at least 50% of all such complexes form by the identifier with the target object, preferably at least 75%, more preferably at most 80% or 90%, still more preferably at most 95%, 96%, 97%, 98% or 99%. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like.

Further, it is advantageous if comparably small amounts of detection molecule are needed. Therefore, in a further preferred embodiment, the molar concentration of the detection molecule is at most 5%, preferably at most 3%, more preferably at most 1%, even more preferably at most 0.5%, most preferably at most 0.1% of the molar concentration of the binding molecule in the sample.

In a yet further preferred embodiment, the concentration of the trapping molecule is in the range of $3*(1$ to $5)$ µmol/l to $5*(1$ to $5)$ µmol/l, such as $3*(1, 2, 3, 4$ or $5)$ µmol/l to $5*(1, 2, 3, 4$ or $5)$ µmol/l, particularly 3 to 5 µmol/l, 3 to 10 µmol/l, 3 to 15 µmol/l, 3 to 20 µmol/l, 3 to 25 µmol/l, 5 to 25 µmol/l, 10 to 25 µmol/l, 15 to 25 µmol/l, as illustrated by Example 2B.

As described above, the method of the present invention is in particular useful for determining the total amount of a certain target (e.g. analyte) in the presence of a binding molecule in particular being an antibody or functionally active part thereof, for example a therapeutically active antibody which is bound to this analyte in a bodily fluid or tissue.

Such therapeutically active antibody may comprise an antibody or functionally active part thereof to which a therapeutic and/or diagnostic moiety is bound covalently or non-covalently. For example, a radionuclide, toxin, cytokine or cytotoxic agent may be bound covalently or non-covalently to the antibody or functionally active part thereof. In case the therapeutic and/or diagnostic moiety is a protein or peptide, the binding molecule may be a fusion protein comprising an antibody or functionally active part thereof. Alternatively, the binding molecule may be therapeutically active as such, e.g. as neutralizing antibody. Therefore, in a yet further preferred embodiment, the binding molecule is or comprises an antibody or functionally active part thereof.

As trapping molecule, an anti-idiotype antibody for the binding molecule (e.g. a therapeutically active antibody or therapeutically active receptor) or functionally active part thereof may be used. An anti-idiotype antibody or functionally active part thereof binds to the binding site of the binding molecule and upon binding, prevents binding of the binding molecule to the analyte. The detection molecule may then bind to the free analyte. Again, such anti-idiotype antibody or functionally active part thereof may comprise further moieties bound covalently or non-covalently to the antibody, as e.g. a diagnostic moiety or means for immobilizing.

Thus, in a yet further preferred embodiment, the trapping molecule is or comprises an anti-idiotype antibody directed against the antigen binding site of the binding molecule or a functionally active part thereof. The generation of anti-idiotype antibodies or functionally active parts thereof is well know to the skilled person and is e.g. described in Sege K et al, PNAS (1978) Vol. 75 No. 5: 2443-2447 and Pan Y. et al, FASEB J. (1995) Vol. 9 No. 1:43-49.

Also, as a detection molecule, an antibody or functionally active part thereof may be used, which is capable of binding to the analyte. The generation of antibodies or functionally active parts thereof is well known, as described below in more detail. Therefore, in a yet further preferred embodiment, the detection molecule is or comprises an antibody or functionally active part thereof.

In preferred methods of the invention, a capture molecule is employed, which carries means for immobilization and is capable of binding to the analyte (see FIG. 1). Again, antibodies and functionally active parts thereof and their generation are well known in the art as described below. Thus, in a yet further preferred embodiment, the capture molecule is or comprises therefore an antibody or a functionally active part thereof, more preferably, the means the capture molecule comprises an antibody or a functionally active part thereof and means for immobilization.

In an also preferred embodiment, the trapping molecule, the binding molecule, the detection molecule and the capture molecule each are or comprise antibodies or functionally active parts thereof.

In a yet further preferred embodiment, the binding molecule is or comprises an antibody, a functionally active part of an antibody, a receptor or a receptor fragment, in particular a therapeutically and/or diagnostically active antibody or therapeutically and/or diagnostically active functionally active part of an antibody or therapeutically and/or diagnostically active receptor or therapeutically and/or diagnostically active receptor fragment. Thus the binding molecule is in a preferred embodiment a therapeutic and/or diagnostic agent.

Thus, in a further preferred embodiment, the trapping molecule, the detection molecule and the capture molecule each are or comprise antibodies or functionally active parts thereof, and the binding molecule is or comprises an antibody, a functionally active part of an antibody, a receptor or a receptor fragment, in particular a therapeutically active antibody or therapeutically active functionally active part of an antibody or therapeutically active receptor or therapeutically active receptor fragment.

An example for a binding molecule comprising a therapeutically active receptor fragment is aflibercept (also called VEGF Trap; Moroney et al. (Future Oncol. (2009); 5(5): 591-600). VEGF Trap is recombinant fusion protein, wherein the binding domain of the soluble VEGF receptor is combined with the Fc fragment of IgG. VEGF Trap binds to all isoforms of VEGF. VEGF-Trap is described to be useful for the treatment of wet macula degeneration and for cancer treatment.

Naturally occurring antibodies are globular plasma proteins (~150 kDa (http://en.wikipedia.org/wiki/Dalton_unit)) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM. In the present invention, examples of suitable formats include the format of naturally occurring antibodies including antibody isotypes known as IgA, IgD, IgE, IgG and IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two beta sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals. Other types of light chains, such as the ι chain, are found in lower vertebrates like Chondrichthyes and Teleostei.

In addition to naturally occurring antibodies, artificial antibody formats including antibody fragments have been developed. Some of them are described in the following.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

Accordingly, the term "antibody", as used herein, means any polypeptide which has structural similarity to a naturally occurring antibody and is capable of specific binding to the respective target, wherein the binding specificity is determined by the CDRs. Hence, "antibody" is intended to relate to an immunoglobulin-derived structure with binding to the respective target including, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which selectively binds to the respective target. The antibody or functionally active parts thereof may be any polypeptide which comprises at least one antigen binding fragment. Antigen binding fragments consist of at least the variable domain of the heavy chain and the variable domain of the light chain, arranged in a manner that both domains together are able to bind to the specific antigen. The "respective target" is the analyte in case of the capture molecule, the binding molecule and the detection molecule, and is the binding molecule in case of the anti-idiotype antibody as preferred trapping molecule.

"Full length" or "complete" antibodies refer to proteins that comprise two heavy (H) and two light (L) chains inter-connected by disulfide bonds which comprise: (1) in terms of the heavy chains, a variable region and a heavy chain constant region which comprises three domains, CH1, CH2 and CH3; and (2) in terms of the light chains, a light chain variable region and a light chain constant region which comprises one domain, CL. With regard to the term "complete antibody", any antibody is meant that has a typical overall domain structure of a naturally occurring antibody (i.e. comprising a heavy chain of three or four constant domains and a light chain of one constant domain as well as the respective variable domains), even though each domain may comprise further modifications, such as mutations, deletions, or insertions, which do not change the overall domain structure.

"Functionally active parts of antibodies" or "antibody fragments" also contain at least one antigen binding fragment as defined above, and exhibit essentially the same function and binding specificity as the complete antibody of which the functionally active part (or fragment) is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

As the first generation of full sized antibodies presented some problems, many of the second generation antibodies comprise only fragments of the antibody. Variable domains (Fvs) are the smallest fragments with an intact antigen-binding domain consisting of one VL and one VH. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides.

A recombinant antibody fragment is the single-chain Fv (scFv) fragment, which is a preferred functionally active part of an antibody according to the invention. In general, it has a high affinity for its antigen and can be expressed in a variety of hosts. These and other properties make scFv fragments not only applicable in medicine, but also of potential for biotechnological applications. As detailed above, in the scFv fragment the VH and VL domains are joined with a hydrophilic and flexible peptide linker, which improves expression and folding efficiency. Usually linkers of about 15 amino acids are used, of which the (Gly4Ser)3 linker has been used most frequently. scFv molecules might be easily proteolytically degraded, depending on the linker used. With the development of genetic engineering techniques these limitations could be practically overcome by research focussed on improvement of function and stability. An example is the generation of disulfide-stabilized (or disulfide-linked) Fv fragments where the VH-VL dimer is stabilized by an interchain disulfide bond. Cysteines are introduced at the interface between the VL and VH domains, forming a disulfide bridge, which holds the two domains together.

Dissociation of scFvs results in monomeric scFvs, which can be complexed into dimers (diabodies), trimers (triabodies) or larger aggregates such as TandAbs and Flexibodies, which also represent functionally active parts of an antibody according to the invention.

Antibodies with two binding domains can be created either through the binding of two scFv with a simple polypeptide link (scFv)2 or through the dimerization of two monomers (diabodies). The simplest designs are diabodies that have two functional antigen-binding domains that can be either the same, similar (bivalent diabodies) or have specificity for distinct antigens (bispecific diabodies). These bispecific antibodies allow for example the recruitment of novel effector functions (such as cytotoxic T cells) to the target cells, which make them very useful for applications in medicine.

Also, antibody formats comprising four variable domains of heavy chains and four variable domains of light chains have been developed. Examples of these include tetravalent bispecific antibodies (TandAbs and Flexibodies, Affimed Therapeutics AG, Heidelberg. Germany). In contrast to a bispecific diabody, a bispecific TandAb is a homodimer consisting of only one polypeptide. Because the two different chains, a diabody can build three different dimers only one of which is functional. Therefore, it is simpler and cheaper to produce and purify this homogeneous product. Moreover, the TandAb usually shows better binding properties (possessing twice the number of binding sites) and increased stability in vivo. Flexibodies are a combination of scFv with a diabody multimer motif resulting in a multivalent molecule with a high degree of flexibility for joining two molecules which are quite distant from each other on the cell surface. If more than two functional antigen-binding domains are present and if they have specificity for distinct antigens, the antibody is multispecific.

In summary, specific immunoglobulin types which represent antibodies or functionally active parts thereof include but are not limited to the following antibody: a Fab (monovalent fragment with variable light (VL), variable heavy (VH), constant light (CL) and constant heavy 1 (CH1) domains), a F(ab')2 (bivalent fragment comprising two Fab fragments linked by a disulfide bridge or alternative at the hinge region), a Fv (VL and VH domains), a scFv (a single chain Fv where VL and VH are joined by a linker, e.g., a peptide linker), a bispecific antibody molecule (an antibody molecule with specificity as described herein linked to a second functional moiety having a different binding specificity than the antibody, including, without limitation, another peptide or protein such as an antibody, or receptor ligand), a bispecific single chain Fv dimer, a diabody, a triabody, a tetrabody, a minibody (a scFv joined to a CH3).

Certain antibody molecules or functionally active parts thereof including, but not limited to, Fv, scFv, diabody molecules or domain antibodies (Domantis) may be stabilized by incorporating disulfide bridges to line the VH and VL domains. Bispecific antibodies may be produced using conventional technologies, specific methods of which include production chemically, or from hybrid hybridomas) and other technologies including, but not limited to, the BiTE™ technology (molecules possessing antigen binding regions of different specificity with a peptide linker) and knobs-into-holes engineering.

Accordingly, an antibody molecule or functionally active part thereof may be a Fab, a Fab', a F(ab')2, a Fv, a disulfide-linked Fv, a scFv, a (scFv)2, a bivalent antibody, a bispecific antibody, a multispecific antibody, a diabody, a triabody, a tetrabody or a minibody.

In another preferred embodiment, the antibody is a monoclonal antibody, a chimeric antibody or a humanised antibody. Monoclonal antibodies are monospecific antibodies that are identical because they are produced by one type of immune cell that are all clones of a single parent cell.

A chimeric antibody is an antibody in which at least one region of an immunoglobulin of one species is fused to another region of an immunoglobulin of another species by genetic engineering in order to reduce its immunogenicity. For example murine VL and VH regions may be fused to the remaining part of a human immunoglobulin. A particular type of chimeric antibodies are humanised antibodies. Humanised antibodies are produced by merging the DNA that encodes the CDRs of a non-human antibody with human antibody-producing DNA. The resulting DNA construct can then be used to express and produce antibodies that are usually not as immunogenic as the non-human parenteral antibody or as a chimeric antibody, since merely the CDRs are non-human.

In a preferred embodiment of the present invention, an antibody molecule or functionally active part thereof used in a method of the invention comprises a heavy chain immunoglobulin constant domain selected from the group consisting of: a human IgM constant domain, a human IgG1 constant domain, a human IgG2 constant domain, a human IgG3 constant domain, a human IgG4 constant domain, a human IgE constant domain, and a human IgA constant domain.

As detailed above in the context with the antibody of the present invention, each heavy chain of a naturally occurring antibody has two regions, the constant region and the variable region. There are five types of mammalian immunoglobulin heavy chain: $\gamma$, $\delta$, $\alpha$, $\mu$ and $\epsilon$, which define classes of immunoglobulins IgM, IgD, IgG, IgA and IgE, respectively.

There are here are four IgG subclasses (IgG1, 2, 3 and 4) in humans, named in order of their abundance in serum (IgG1 being the most abundant). Even though there is about 95% similarity between their Fc regions of the IgG subclasses, the structure of the hinge regions are relatively different. This region, between the Fab arms (Fragment antigen binding) and the two carboxy-terminal domains CH2 and CH3 of both heavy chains, determines the flexibility of the molecule. The upper hinge (towards the amino-terminal) segment allows variability of the angle between the Fab arms (Fab-Fab flexibility) as well as rotational flexibility of each individual Fab. The flexibility of the lower hinge region (towards the carboxy-terminal) directly determines the position of the Fab-arms relative to the Fc region (Fab-Fc flexibility). Hinge-dependent Fab-Fab and Fab-Fc flexibility may be important in triggering further effector functions such as complement activation and Fc receptor binding. Accordingly, the structure of the hinge regions gives each of the four IgG classes their unique biological profile.

The length and flexibility of the hinge region varies among the IgG subclasses. The hinge region of IgG1 encompasses amino acids 216-231 and since it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, it is relatively short and contains a rigid poly-proline double helix, stabilised by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3 the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2.

Using the methods of the invention, the total amount and/or concentration of a wide variety of analytes may be detected. For example, the analyte may be any chemical compound. As explained above, the methods of the invention are in particular useful for detecting an analyte which is the target of a therapeutically active antibody or functionally active part of an antibody or receptor or receptor fragment, and wherein such therapeutically active antibody or functionally active part of an antibody or receptor or receptor fragment represents the binding molecule of the invention. Such target may be a hormone, peptide or protein, a molecule circulating in the blood of an animal or human or a biomarker, in particular a tumor marker. Therefore, in a further preferred embodiment, the analyte is a chemical compound, preferably a hormone, peptide or protein, a molecule circulating in the blood of an animal or human or a biomarker, in particular a tumor marker.

In one also preferred embodiment, the analyte is a protein.

As disclosed above, in a preferred embodiment of the present invention, detecting the detection molecule-analyte complex is performed in a non-competitive assay, particularly in a sandwich assay, especially wherein the sandwich assay employs a capture molecule capable of binding to the analyte, and wherein the capture molecule carries means for immobilization, and the detection molecule and the capture molecule bind to different, non-overlapping epitopes on the analyte.

In a yet further preferred embodiment, the detection molecule carries means for detectable labeling with a detectable label, particularly means for direct or indirect detection.

The term "detectable label" as used herein refers to any substance that is capable of producing a signal for direct or indirect detection. The detectable label thus may be detected directly or indirectly. For direct detection label suitable for use in the present invention can be selected from any known detectable marker groups, like chromogens, fluorescent groups, chemiluminescent groups (e.g. acridinium esters or dioxetanes), electrochemiluminescent compounds, catalysts, enzymes, enzymatic substrates, dyes, fluorescent dyes (e.g. fluorescein, coumarin, rhodamine, oxazine, resorufin, cyanine and derivatives thereof), colloidal metallic and nonmetallic particles, and organic polymer latex particles. Other examples of detectable labels are luminescent metal complexes, such as ruthenium or europium complexes, e.g. as used for ECLIA, enzymes, e.g. as used for ELISA, and radioisotopes; e.g. as used for RIA.

Indirect detection systems comprise, for example, that the detection molecule, e.g. an antibody or functionally active fragment thereof, is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Also preferred are haptens like digoxin and biotin and analogues thereof. The second partner of such binding pair, e.g. an antibody, streptavidin, etc., usually is labeled to allow for direct detection, e.g. by the detectable labels as mentioned above.

For a non-competitive assay or sandwich assay, two different antibodies or functionally active fragments thereof are needed, which bind to the same antigen and which do not hinder each other when binding to the antigen. Non-competitive assays or sandwich assays are advantageous over competitive assays due to their higher sensitivity. In case of a sandwich assay, one of the antibodies, in this case the capture molecule can be immobilized to a support. Upon addition of a probe solution, the antigen therein (i.e. the analyte according to the invention) binds to the capture molecule, and the detection molecule can bind to a different binding site of the analyte (see FIG. 1B). For detection of the detection molecule—analyte complex, the detection molecule is used, as explained above in detail. As both the detection molecule and the capture molecule have to bind to the analyte in this embodiment of the invention, both molecules bind to different, non-overlapping epitopes on the analyte in this embodiment. An epitope, also known as antigenic determinant, is the part of an antigen that is recognized by binding molecules, in particular antibodies or functionally active parts thereof. The part of an antibody that recognizes the epitope is also called a paratope. The epitopes of protein antigens are divided into two categories, conformational epitopes and linear epitopes, based on their structure and interaction with the paratope. Methods for determining epitopes are known in the art and comprise e.g. epitope mapping e.g. using protein microarrays, and with the ELISPOT or ELISA techniques. Epitopes of proteins typically comprise several amino acids, in case of linear epitopes typically a stretch of 5 to 15 amino acids. In order to avoid sterical hindrance, it is therefore preferred, that the epitopes of the capture molecule and the detection molecule are non-overlapping, i.e. completely separate with regard to the primary structure in case of linear epitopes.

In a preferred embodiment, the sandwich assay is a sandwich immunoassay, in particular, an enzyme-linked immunoassay (ELISA). An immunoassay is a biochemical test that measures the presence or concentration of a macromolecule in a solution through the use of an antibody or functionally active fragment thereof. The molecule detected by the immunoassay is often referred to as an "analyte" and is in many cases a protein. Immunoassays come in a many different formats and variations. Immunoassays may be run in multiple steps with reagents being added and washed away or separated at different points in the assay. Multi-step assays are often called separation immunoassays or heterogeneous immunoassays. Some immunoassays can be carried out simply by mixing the reagents and sample and making a physical measurement. Such assays are called homogenous immunoassays.

The use of a calibrator is often employed in immunoassays. Calibrators are solutions that are known to contain the analyte in question, and the concentration of that analyte is generally known. Comparison of an assay's response to a real sample against the assay's response produced by the calibrators makes it possible to interpret the signal strength in terms of the presence or concentration of analyte in the sample.

Suitable sandwich assays other than ELISA are (electro-) chemo luminescence immunoassay (ECLIA), radioimmunoassay (RIA), fluorescence immunoassay (FIA), Microparticle capture enzyme immunoassay (MEIA), Solid-phase fluorescence immunoassays (SPFIA), Particle concentration fluorescence immunoassay (PCFIA), Nephelometric and Turbidimetric assay with and without latex particle enhancement (LPIA). Also, the assay may be in the form of test strips.

It is known to skilled person, that the detectable label and the capture molecule, where applicable, will be chosen according to the non-competitive assay, in particular sandwich assay chosen, and vice versa.

In a further preferred embodiment, the proteins in the sample are not denatured before or during the method of the invention. This ensures that the binding properties of the various binding molecules and the three-dimensional structure of the analyte employed in the method of the invention are maintained. In a further preferred embodiment, the proteins in the sample are not irreversibly denatured before or during the method of the invention. In case a reversible denaturing step was employed before the first step of the method of the invention, denaturing should be reversed prior to the method, in order to ensure that the binding events can occur properly. In a further preferred embodiment, the analyte is a protein which is not denatured before or during the method of the invention. In a further preferred embodiment, the analyte is a protein which is not irreversibly denatured before or during the method of the invention. In a further preferred embodiment, the detection molecule, and/or trapping molecule and/or binding molecule, and/or capture molecule where applicable is/are a protein which is not denatured before or during the method of the invention.

The advantage of the methods of the invention is that the total amount of analyte can be determined in the presence of the binding molecule which is capable of binding to the analyte. Therefore, it is not required to perform a washing step, in particular in order to remove the binding molecule. Therefore, in a preferred embodiment, no washing step is performed after step (i) of the invention.

Alternatively, a washing step may be performed. Such washing step may be performed e.g. in case of the preferred embodiment illustrated in FIG. 1, wherein the analyte is immobilized via binding to the capture molecule. In such embodiment, the complex of binding molecule and trapping molecule may be washed away prior to detecting the detection molecule-analyte complex. However, it is understood, that it is also possible to detect detection molecule-analyte complex without a prior washing step in such embodiment. Such washing step, if performed, can be performed as known by a skilled person, in particular using a buffered solution, which preferably does not perturb binding of complexes formed during the method of the invention.

Thus, in a further embodiment, a washing step is performed after step (i) of the invention. Preferably, no washing step is performed after step (i) of the invention.

The methods of the invention may be used for various types of samples, preferably wherein the sample is a liquid, in particular a bodily liquid. Thus, in a further embodiment of the present invention, the sample is a liquid, in particular an aqueous liquid, blood or blood serum.

In a further preferred embodiment, the concentration of the analyte in the sample, in particular blood or blood serum, is in the range of 1 pg/ml to 20 µg/ml, preferably 1 ng/ml to 10 µg/ml.

As disclosed above, the binding molecule is in a preferred embodiment a therapeutic and/or diagnostic agent, in particular a therapeutic agent. Such therapeutic and/or diagnostic agents are often expensive, and moreover, the efficacy and pharmacokinetic of such therapeutic and/or diagnostic agents may differ considerably from subject to subject. Therefore, it would be helpful to determine the analyte in samples from a subject, thereby determining the therapeutic success and/or disease progression, as well as absence, presence and/or severity of a disease of a patient.

Therefore, in a further preferred embodiment, the binding molecule, particularly a therapeutic or diagnostic agent, has been administered to the subject from whom the sample has been obtained. The administration of the binding molecule depends on the nature of the binding molecule and a physician will adapt the mode, dosage regimen and dose of administration accordingly. Typically, a therapeutically effective amount will be administered in case of a therapeutically active binding molecule. Thus, the method may be used to determine or monitor the amount or concentration of the therapeutic or diagnostic agent in the subject.

Alternatively, the binding molecule is not a therapeutic agent, but e.g. a diagnostic agent or a naturally occurring binding partner of the analyte. Preferably, the analyte is a biomarker. Also in this situation, the determination of the total amount and/or concentration of the analyte allows monitoring the disease and responsiveness of the disease to a treatment.

Moreover, it is also often advantageous not only to determine the total amount of analyte, but in addition to determine the amount of free analyte, bound analyte and/or the ratio of bound vs. free and/or total analyte or free vs. bound and/or total analyte. This is further useful for monitoring the disease and responsiveness of the disease to the treatment.

In particular, it is often important to determine the amount of analyte bound to the binding molecule, and or to determine the ratio of amount (or concentration, respectively) of analyte bound to the binding molecule vs. the amount (or concentration, respectively) of total analyte or free analyte. Such amount or ratio is important for monitoring therapy of a disease, in particular therapy of a disease with the binding molecule being a therapeutic agent.

Therefore, in a yet further preferred embodiment, the method of the invention comprises
  i) performing step (i) as defined above;
  ii) performing step (ii) as defined above; and
  iii) additionally determining—in the absence of trapping molecule—the amount and/or concentration of free analyte in the sample, which is not bound to the binding molecule, and optionally, determining the amount and/or concentration and/or the ratio of analyte bound to the binding molecule in the sample.

In case of a binding molecule being a therapeutic agent, the analyte preferably represents the target of treatment with the binding molecule; alternatively, the analyte is a biomarker for a certain disease. A reduced amount and/or concentration of the analyte may therefore indicate that the disease is not present anymore or less severe. Similarly, an increased amount and/or concentration of the analyte may therefore indicate that the disease is present or more severe. In particular, the presence or absence of a disease of a patient may be determined by determining whether the total amount and/or concentration of the analyte is above or below a certain cut-off value for a certain analyte in a certain disease. Therefore, in a preferred embodiment of the present invention, the total amount and/or concentration of the analyte is indicative for the absence, presence and/or severity of a disease of a patient. Therefore, in a further preferred embodiment of the present invention, the total amount and/or concentration of the analyte is indicative for the therapeutic response of a patient to a treatment, in particular wherein the patient has been treated with the binding molecule.

In a yet further preferred embodiment of the present invention, the amount and/or concentration and/or the ratio of analyte bound to the binding molecule in the sample is indicative for the absence, presence and/or severity of a disease of a patient, and/or the therapeutic response of a patient to a treatment, in particular wherein the patient has been treated with the binding molecule.

Using the methods of the invention, a therapy in particular with a binding molecule being a therapeutic agent can be monitored, thereby allowing adaption of therapy if necessary. This is in particular helpful in diseases like cancer. Therefore, in a further preferred embodiment of the present invention, the method is used for monitoring therapy, particularly in cancer therapy. In one embodiment, therapy, in particular cancer therapy, is performed with the binding molecule as therapeutic agent and/or using therapies known in the art. In case of cancer, known therapies comprise chemotherapeutic treatment, in particular treatment with cytotoxic compounds like taxanes, and/or radiation therapy.

In another aspect, the present invention relates to a kit or composition suitable for determining the total amount and/or concentration of an analyte in a sample, which sample further comprises a binding molecule capable of binding to the analyte, comprising:
  a) a detection molecule capable of forming a complex with the analyte; and
  b) a trapping molecule directed against the binding site of the binding molecule; and
  c) optionally the analyte; and
  d) optionally the binding molecule capable of binding to the analyte; and
  e) optionally a capture molecule carries means for immobilization of the analyte, wherein the detection molecule is different from the binding molecule, and wherein the analyte is different from the trapping molecule, and wherein the detection molecule is only capable of forming a complex with the analyte when the analyte is not bound by the binding molecule.

Such kit may be used in a method of the invention described above. In a preferred embodiment, the kit or composition of the invention is suitable for use in any of the methods of the invention. Also, all embodiments disclosed as preferred embodiments for methods of the invention, also apply to the kits of the invention.

Thus, in yet another aspect, the present invention relates to the use of a kit or composition of the invention in any of the methods of the invention. In particular, the total amount of an analyte may be determined, as described above. In a preferred embodiment, the analyte is different from the trapping molecule. In a further preferred embodiment, the detection molecule is only capable of forming a complex with the analyte when the analyte is not bound by the binding molecule. Therefore, in yet another aspect, the present invention relates to the use of a kit or composition of the invention for determining the total amount and/or concentration of an analyte in a sample, preferably wherein the analyte is different from the trapping molecule and/or wherein the detection molecule is only capable of forming a complex with the analyte when the analyte is not bound by the binding molecule. Preferably, the analyte is a biomarker, and/or the sample is blood or blood serum.

Also, the therapeutic response of a patient to a treatment, in particular wherein the patient is treated with the binding molecule may be determined using the kits of invention, by employing them in methods of the invention. Therefore, in yet another aspect, the present invention relates to the use of a kit or composition of the invention for determining the therapeutic response of a patient to a treatment, in particular wherein the patient is treated with the binding molecule.

EXAMPLES

Example 1: Method of the Invention Wherein the Binding Molecule is a Therapeutically Active Antibody, and the Trapping Molecule is an Anti-Idiotype Antibody (Anti-Id Ab)

A common maximum antibody (IgG, 150 kDa) concentration in viscosity formulation testing is 150 mg/ml=1 mM antibody. E.g. stable Herceptin (as therapeutically active antibody) concentration in patient sera at a weekly Herceptin dosage of 500 mg Herceptin is 377 µg/ml=2.6 µM Herceptin, and Pertuzumab 200 µg/ml=1.4 µM (both antibodies bind to HER2/neu, representing the analyte according to the invention). The concentration difference between a maximum dosage and a common serum concentration value can be regarded as a window for the application concentration of an anti-id Ab in order to determine total analyte in a sample in vitro (in the present example, the analyte is HER2). 1 mM anti-id Ab is a very high possible application concentration, but due to cost effectiveness, much lower anti-id antibody concentrations are preferred. Furthermore, the anti-id Ab concentration must be high enough to shift the reaction into equilibrium during the typical incubation time in electrochemoluminescence measurements, in particular using Elecsys® (Roche).

Estimation for time to equilibrium (T): T=3.5/(ka*c)+kd 9 min incubation time in the Elecsys® system is regarded as no limiting factor for an anti-id-antibody binding with 1.3 nM affinity, a common kinetic rate profile and 1 μM concentration.

Kinetic competition assays, preferably via surface plasmon resonance, in particular using the Biacore® system, are usually driven with a 3-fold to 5-fold molar excess of the respective competitor over the target. The anti-id antibody should not be applied below a concentration [therapeutically active antibody]*3=[Anti-id-Ab]. In case of blocking serum Herceptin with an anti-id antibody, the anti-id Ab concentration should be 5*2.6 μM=13 μM (2 mg/ml) anti-id Ab, which is feasible and fulfills the time to equilibrium requirements.

Example 2: Applications Useful Also for Extremely High Affinity Binding Molecules A robust algorithm for the application concentration of trapping molecules could be complemented by an affinity quotient:

Example A $(KD_{(trapping\ molecule)}/KD_{(binding\ molecule)})*5\ \mu M=[\text{Anti-id-Ab}]$ $(KD_{anti-Herceptin}\ 1\ nM/KD_{Herceptin}\ 0.1\ nM)*5\ \mu M=50\ \mu M=7\ mg/ml\ \text{Anti-id-Ab}$ Example B, adding the serum binding molecule concentration:

$(KD_{(trapping\ molecule)}/KD_{(binding\ molecule)})*[\text{serum binding molecule}]*3=[\text{Anti-id-Ab}]$.

$(KD_{anti-Herceptin}\ 1\ nM/KD_{Herceptin}\ 0.1\ nM)*2.6\ \mu M_{serum\ Herceptin}*3=78\ \mu M=11\ mg/ml\ \text{Anti-id-Ab}$ A 3-fold molar excess factor of the Anti-id-Ab vs. binding molecule is sufficient, because the Anti-id-Ab concentration increases by the multiplication with the affinity quotient.

Example C $(KD_{anti-AbxY}\ 1\ nM/KD_{AbxY}\ 0.01\ nM)*2.6\ \mu M_{serum\ Abxy}*3=780\ \mu M=111\ mg/ml$ Example C is feasible, however not cost-effective. A higher affine trapping molecule is preferred.

Another very important aspect is the binding valences of the binding molecules, in particular antibodies. When binding to small targets, a binding molecule being an antibody typically shows a binding valence of MR=2, whereas for sterical reasons the trapping molecule being an anti-idiotype antibody mostly shows a binding valence of MR=1 and smaller. In this case, the functional molarity quotient preferably needs to be considered within the calculation.

Example D $(MR_{(binding\ molecule)})/MR_{(trapping\ molecule)})*(KD_{(Anti-id-Ab)}/KD_{(binding\ molecule)})*[\text{serum binding molecule}]*3=[\text{Anti-id-Ab}]$ $(MR_{(binding\ molecule)}\ 2/MR_{(Anti-id-Ab)}\ 1)*(KD_{(Anti-id-Ab)}\ 1\ nM/KD_{(binding\ molecule)}\ 0.1\ nM)*[2.6\ \mu M]*3=156\ \mu M$ 22 mg/ml trapping molecule being an anti-id antibody is required.

Example D represents a preferred embodiment according to the invention.

Example 3A: Generation of Monoclonal Antibodies

For the generation of antibodies against TWEAK, Balb/C, NMRI and SJL mice were immunized with recombinant E. coli derived TWEAK protein. All mice were subjected to 3 immunizations at the time points 0, 6 and 10 weeks after start of the immunization campaign. At each time point each mouse was immunized with 100 μg immunogen dissolved in 100 μl PBS. For the first immunization the immunogen was mixed with 100 μl CFA. For the second and third immunization the immunogen was mixed with 100 μl IFA. The first and the third immunization were applied via the intraperitoneal route and the second immunization was applied subcutaneously. 2 and 3 days prior to the preparation of splenocytes for antibody development using hybridoma technology, the mice were subjected to intravenous booster immunizations with 12.5 μg immunogen in 100 μl PBS and without adjuvant.

For the determination of serum titers against the respective immunogen a small amount of serum of each mouse was collected in week 11 after start of the immunization. For the ELISA recombinant TWEAK was immobilized on the plate surface. For the immobilization the immunogen was used at a concentration of 0.25 μg/ml. The serum from each mouse was diluted in PBS with 1% BSA and the dilutions were added to the plates. The sera were tested at dilutions 1:300, 1:900, 1:2700, 1:8100, 1:24300, 1:72900, 1:218700 and 1:656100. Bound antibody was detected with a HRP-labeled F(ab')$_2$ goat anti-mouse Fcγ (Dianova) and ABTS (Roche) as a substrate.

In Table 1 the serum titers of the immunized mice are shown. The analyte, E. coli derived recombinant human TWEAK, was immobilized at a concentration of 250 ng/ml. The serum titers were measured by serial dilutions of the individual mouse sera on 96 well plates.

TABLE 1

| Mouse strain | Mouse number | Serum titer |
|---|---|---|
| Balb/c | 1831/1 | 48788 |
| Balb/c | 1831/2 | 61589 |
| Balb/c | 1831/3 | 33658 |
| Balb/c | 1831/4 | 39573 |
| Balb/c | 1831/5 | 72775 |
| NMRI | 1832/1 | 3460 |
| NMRI | 1832/2 | 51925 |
| NMRI | 1832/3 | 64945 |
| NMRI | 1832/4 | 24769 |
| NMRI | 1832/5 | 3664 |
| SJL | 1833/1 | 25774 |
| SJL | 1833/2 | 30777 |
| SJL | 1833/3 | 23692 |
| SJL | 1833/4 | 55638 |
| SJL | 1833/5 | 49018 |

Antibodies were developed with hybridoma technology by fusing primary B-cells with P3X63Ag8.653 myeloma cells. 2 days after the final booster immunization, immunized mice were sacrificed and spleen cell populations were prepared. The splenocytes were fused with P3X63Ag8.653 by using PEG fusion. The cellular batch culture from the fusion was incubated overnight at 37° C. under 5% $CO_2$. The following day the cellular batch, containing fused cells was centrifuged for 10 min at 400 g. Thereafter, the cells were suspended in hybridoma selection media supplemented with 0.1× azaserine-hypoxanthine (Sigma) and were seeded at a concentration of $2.5 \times 10^4$ cells per well in 96-well plates. The plates were cultured for at least 1 week at 37° C. under 5% $CO_2$. 3 days prior to ELISA analysis the selection media was changed.

Primary culture supernatants were tested in ELISA against recombinant TWEAK antigen, immobilized on the plate surface. Recombinant TWEAK was immobilized at a concentration of 0.25 μg/ml. Hybridoma Supernatant was added to the plates and incubated for 1 h at room temperature. Bound antibody was detected with a HRP-labeled F(ab')$_2$ goat anti-mouse Fcγ (Dianova) and ABTS (Roche) was used as a HRP-substrate.

Table 2 shows the evaluation of the selected clones by ELISA. The binding of the selected clones against recombinant human TWEAK was tested in ELISA. The analyte was immobilized on the plate surface at a concentration of 0.25 μg/ml. All clones show binding to human TWEAK.

TABLE 2

| Clone number | TWEAK ELISA [OD] |
| --- | --- |
| 10.180.3 | 1.39 |
| 10.43.14 | 1.19 |
| 10.156.32 | 1.50 |
| 10.209.34 | 1.14 |
| 10.250.35 | 1.28 |
| 10.10.36 | 1.08 |
| 10.217.66 | 1.31 |
| 10.61.71 | 1.08 |
| 10.230.79 | 1.04 |
| 11.226.1 | 1.429 |

Example 3B: Generation of Monoclonal Anti-Idiotypic Antibodies a) Immunization of Mice NMRI mice were primarily immunized intraperitoneally with 100 μg F(ab')$_2$ of the humanized monoclonal anti-TWEAK antibody formulated with CFA (Complete Freund's Adjuvant). Two further intraperitoneal immunization steps followed after 6 and 10 weeks, with application of 100 μg of the above mentioned F(ab')$_2$ per mouse mixed with IFA (Incomplete Freund's Adjuvant). Subsequently, mice were boosted by i.v. administration of 25 μg F(ab')$_2$ (in PBS) 3 days before animals were sacrificed and spleen cells were isolated and used for fusion.

b) Fusion and Cloning

Fusion of the spleen cells with myeloma cells was performed by standard procedures using polyethylene glycol. Briefly, approx. $1 \times 10^8$ splenocytes were mixed with approx. $2 \times 10^7$ myeloma cells (P3x63-Ag8.653, ATCC CRL1580) in RPMI-1640 and centrifuged (10 min. at 510× g and 4° C.). The cells were washed once with RPMI-1640 and centrifuged again. Thereafter, 1 ml of PEG (polyethylene glycol, molecular weight 4,000 g/mol) was added, mixing was done by the pipetting. After 1 min. in a water bath at 37° C., 5 ml of RPMI-1640 were added drop wise, the suspension was mixed, filled to 30 ml with RPMI-1640 and centrifuged. Cells were resuspended in selection medium (RPMI-1640 supplemented with 10% FCS, 100 U/ml IL-6, 2 mM L-glutamine, 100 μM NEAA, 1 mM sodium pyruvate, 24 μM 2-mercaptoethanol, 100 μM hypoxanthine and 1 μg/ml azaserine) and subsequently plated into 96-well cell culture plates. After approximately 10 days, the primary cultures were assayed for production of specific antibodies (as described below). Primary cultures exhibiting binding to the above-mentioned humanized F(ab')2 and no cross-reactivity with normal human IgG were cloned by single cell sorting using a flow cytometer (FACSAria, BD Biosciences). Cell clones were grown in RPMI-1640 supplemented with 10% FCS, 50 U/ml IL-6, 2 mM L-glutamine, 100 μM NEAA, 1 mM sodium pyruvate and 24 μM 2-mercaptoethanol. The established monoclonal hybridoma cell lines were re-tested for specificity as described below.

For preservation hybridoma cell lines were frozen in freezing medium (92.5% FCS, 7.5% DMSO) at −80° C. using a freezing container (rate of cooling −1° C./minute) (Mr. Frosty, Nalgene) and subsequently stored in liquid nitrogen.

Example 4: Screening Assays for Detection of Anti-Idiotypic Antibodies a) Primary Screening for Antibodies Binding Preferentially to the Humanized anti-TWEAK mAb For the determination of the specificity of the antibodies in the culture supernatants of the hybridoma cells, MTPs (microtiter plates) pre-coated with recombinant streptavidin (MicroCoat, Bernried, Germany) were coated with 100 μl/well of the biotinylated F(ab')$_2$ fragment of the humanized anti-TWEAK mAb (250 ng/ml) or biotinylated polyclonal human IgG (2 μg/ml). Antibodies were diluted in PBS/1.0% BSA II (Roche). For efficient coating the plates were incubated for 1 h at RT with the respective antibody solution. Subsequently, the plates were washed with 0.9% NaCl/ 0.05% Tween-20®. In the next step, 100 μl/well of the antibody solution to be assayed (culture supernatants) were added and incubated for 1 h at RT. After washing with 0.9% NaCl/0.05% Tween-20®, 100 μl/well of a horseradish peroxidase-labeled F(ab')$_2$ fragment of a polyclonal sheep anti-mouse Fcγ antibody (100 ng/ml) were added for the detection of bound sample antibody. After incubation for 1 h at RT plates were washed as described above. Finally, 100 μl/well of ABTS® (Roche) were added. After 30 min. incubation at RT the extinction (OD) was measured at 405 nm and 492 nm [405/492].

This screening led to a selection of antibodies binding to the humanized anti-TWEAK mAb as well as exhibiting only low or no cross-reactivity to human IgG. This selection of antibodies was further subjected to assay b).

b) Selection of Antibodies with the Lowest Cross Reactivity to Human IgG

In order to identify from the candidates of screening b) those that exhibit the lowest cross-reactivity to human IgG, the following assay was performed. MTPs pre-coated with recombinant streptavidin (MicroCoat) were coated with 100 μl/well of the biotinylated F(ab')$_2$ fragment of the humanized anti-TWEAK mAb (250 ng/ml in PBS/1.0% BSA II) as described above. Subsequently, coated plates were washed with 0.9% NaCl/0.05% Tween-20®. In the next step, a mixture of 50 μl of the candidate antibody (culture supernatant) and 50 μl polyclonal human IgG (at a final concentration of 40 mg/ml) was added to the wells. In a control experiment, a mixture of 50 μL of the respective candidate antibody (culture supernatant) and 50 μl buffer was added to the wells. Plates were incubated 1 h at RT. After washing with 0.9% NaCl/0.05% Tween-20®, 100 μl/well of a horseradish peroxidase-labeled F(ab')$_2$ fragment of a polyclonal sheep anti-mouse Fcγ antibody (100 ng/ml) were added for the detection of bound sample antibody. After incubation for 1 h at RT plates were washed as described above. Finally, 100 μl/well of ABTS® (Roche Diagnostics GmbH) were added. After 30 min. incubation at RT the extinction (OD) was measured at 405 and 492 nm [405/492].

Antibodies exhibiting the least loss of assay signal in the presence of polyclonal human IgG show the lowest cross-reactivity and were selected for further evaluation.

c) Interaction Analysis

The kinetic and affinity of the interaction of the different murine anti-idiotypic mAbs with the humanized anti-TWEAK antibody as wells as the cross-reactivity with normal polyclonal human IgG was evaluated by Biacore analysis. Briefly, a CM5 sensor chip (GE Healthcare) coated with an anti-mouse Fcγ antibody was used to capture the murine anti-idiotypic mAbs. The Fab fragment of the humanized anti-TWEAK antibody was used as analyte at the following concentrations: 0.04 nM, 0.12 nM, 0.37 nM, 1.11 nM, 3.33 nM and 10 nM. To evaluate the cross-reactivity of the anti-idiotypic mAbs with normal human IgG, a 1000 nM solution of polyclonal human IgG was used as analyte. All experiments were performed at 37° C. using a Biacore A100 system (GE Healthcare); the association and dissociation were recorded for 180 sec or 300 sec, respectively. Antibodies with the highest affinity and no detectable cross-reactivity with normal human IgG were selected for further use.

TABLE 3

| Clone No. anti-Id mAb | ka (1/Ms) | kd (1/s) | t/2 diss [min] | KD (pM) | Cross-reactivity human IgG |
|---|---|---|---|---|---|
| 5.4.1 | >1.00E+06 | 3.18E−05 | 363 | <32 | not detectable |
| 5.5.1 | >1.00E+06 | 2.44E−04 | 47 | <244 | not detectable |
| 5.10.4 | >1.00E+06 | 1.41E−04 | 82 | <141 | not detectable |
| 5.11.4 | >1.00E+06 | 2.44E−05 | 474 | <24 | not detectable |
| 5.12.6 | >1.00E+06 | 3.18E−05 | 364 | <32 | not detectable |
| 5.13.6 | >1.00E+06 | 3.05E−05 | 379 | <30 | not detectable |
| 5.17.11 | >1.00E+06 | 1.63E−05 | 709 | <16 | not detectable |
| 5.19.11 | >1.00E+06 | 1.49E−05 | 777 | <15 | not detectable |
| 5.25.20 | >1.00E+06 | 1.90E−05 | 609 | <19 | not detectable |
| 5.28.20 | >1.00E+06 | 1.96E−05 | 589 | <20 | not detectable |
| 5.36.37 | >1.00E+06 | 3.18E−05 | 364 | <32 | not detectable |
| 5.38.37 | >1.00E+06 | 3.79E−05 | 305 | <38 | not detectable |

Table 3 shows the kinetic and affinity of the interaction of the different murine anti-idiotypic mAbs (Clone No. anti-Id mAb) with the humanized anti-TWEAK antibody as wells as the cross-reactivity with normal polyclonal human IgG (Cross-reactivity human IgG).

Example 5: Detection of Soluble TWEAK (10.180.003-IgG-Bi/11.226.001-IgG-Ru)

An electrochemiluminescence immunoassay (ECLIA) for the specific measurement of TWEAK in human serum or plasma samples was developed using the cobas® analyzer e411.

The cobas® TWEAK immunoassay is an electrochemiluminescence immunoassay (ECLIA) that functions via the sandwich principle. There are two antibodies included in the assay—a biotinylated monoclonal antibody 10.180.003-IgG-Bi (capture antibody) and a ruthenylated monoclonal anti-TWEAK antibody 11.226.001-IgG-Ru (detection antibody)—which form sandwich immunoassay complexes with TWEAK in the sample. The complexes are then bound to solid-phase streptavidin-coated microparticles. The microparticles are magnetically captured onto the surface of an electrode, and the application of a voltage to the electrode induces chemiluminescent emission, which is measured by a photomultiplier for readouts. Results are determined via an instrument-specific calibration curve. For the detection of total TWEAK an anti-idiotypic monoclonal antibody (MAK<ID<<TWEAK>5.38.37-IgG) is used. This antibody is incubated with the sample on the cobas® analyzer e411 prior to addition of the sandwich monoclonal antibodies (10.180.003-IgG-Bi-11.226.001-IgG-Ru).

The assay is applied as described in the cobas® analyzer e411 operation manual, allowing 36 minutes incubation of 35 µl of the sample with 35 µl of reagent 1 (R1) containing 35 mg/ml of MAK<ID<<TWEAK>5.38.37-IgG in reaction buffer for the detection of total TWEAK. For the detection of free TWEAK the same buffer R1 without the anti-ID monoclonal antibody MAK<ID<<TWEAK>5.38.37-IgG is used. The mixture is then incubated for 9 minutes with 95 µl of reagent 2 (R2) containing 0.68 µg/ml biotinylated 10.180.003-IgG-Bi and 0.68 g/ml ruthenylated 11.226.001-IgG-Ru in the same reaction buffer and 35 µl of a microparticle suspension. During incubation an antibody-analyte-antibody sandwich is formed that is bound to the microparticles. Finally, the microparticles are transferred to the detection chamber of the cobas® analyzer e411 for signal generation and readout. For calibration a series of calibrators with different concentrations of recombinant TWEAK (PeproTech) (0 ng/ml, 0.037 ng/ml, 0.111 ng/ml, 0.333 ng/ml, 1 ng/ml and 3 ng/ml) is prepared in calibration matrix (50 mM Tris/HCl; 25 mM L-Asn; pH 7.5). The equation of the calibration curve was calculated by non-linear least-squares curve-fitting (RCM-Rodbard) and used for converting the signal readout into the corresponding concentration value.

Example 6: Detection of Total TWEAK

Figure 2:
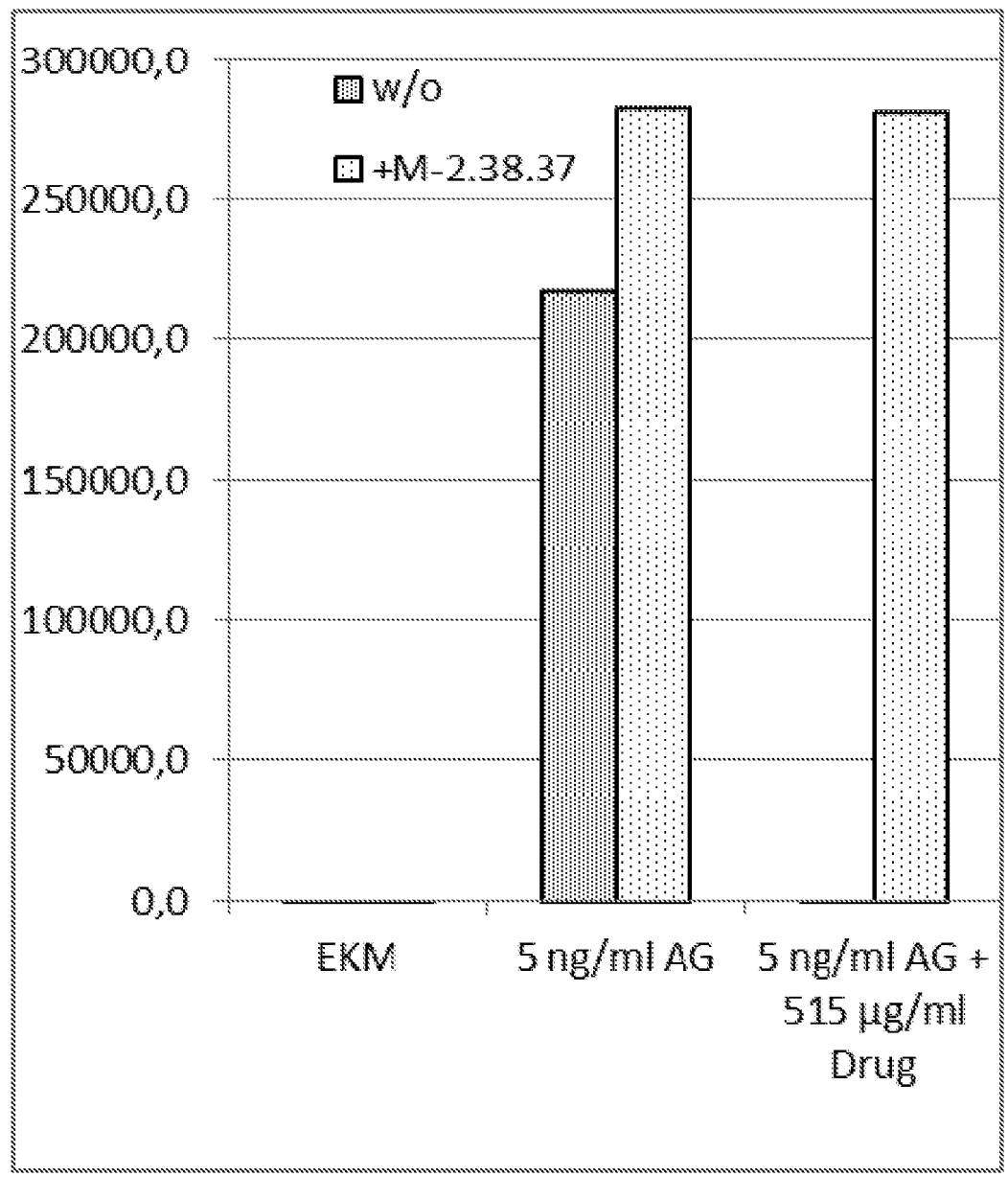
FIG. 2: represents the results according to Example 4 (Detection of total TWEAK). Artificial matrix (EKM); 5 ng/ml of recombinant TWEAK (5 ng/ml AG); 5 ng/ml of recombinant TWEAK spiked with 515 µg/ml of the therapeutic antibody (5 ng/ml AG+515 µg/ml Drug). Results are shown for samples without anti-idiotypic antibody (w/o) and with a large excess of anti-idiotypic antibody (+M−2.38.37).
Figure 3:
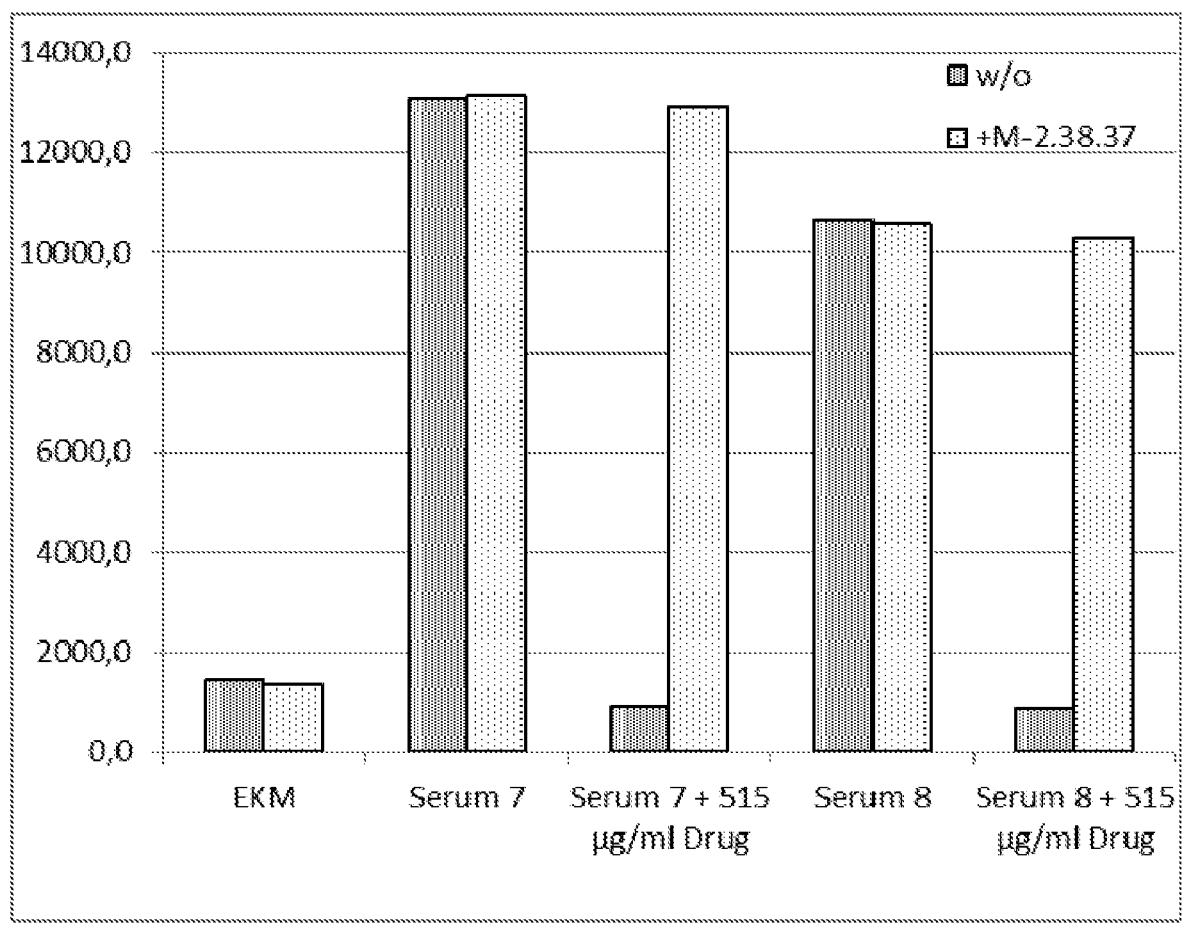
FIG. 3: represents the results according to Example 4 (Detection of total TWEAK). Artificial matrix (EKM); Serum samples (Sample 7 and Sample 8, respectively); Serum samples containing the therapeutic antibody (Sample 7+515 µg/ml Drug and Sample 8+515 µg/ml Drug, respectively); Results are shown for samples without anti-idiotypic antibody (w/o) and with a large excess of anti-idiotypic antibody (+M−2.38.37).

To assess the effect of the presence of the drug compound, the artificial matrix (EKM) with 5 ng/ml of recombinant (rec.) TWEAK (results shown in FIG. 2) and two native samples (results shown in FIG. 3), respectively, were spiked with 515 µg/ml of the drug compound. Results for samples without anti-idiotypic antibody (w/o) and with a large excess of anti-idiotypic antibody (M−2.38.37) were compared.

While there is no signal detectable in samples containing the therapeutic antibody, the signal level can be restored to the level of a sample without therapeutic antibody by addition of anti-idiotypic antibody. This holds true for spiked buffer as well as for spiked serum samples. By this means it is possible to determine free and total target (independent of the previous binding of the therapeutic antibody) from one single sample tube in a single run.

The invention claimed is:

1. A kit or composition suitable for determining the total amount and/or concentration of an analyte in a sample, which sample further comprises a binding molecule capable of binding to the analyte, comprising:
   a) a detection molecule capable of forming a complex with the analyte; and
   b) a trapping molecule directed against the binding site of the binding molecule, wherein the trapping molecule is an anti-idiotypic antibody; and
   c) optionally the analyte, wherein, if present, the analyte is a protein; and
   d) optionally the binding molecule capable of binding to the analyte, wherein, if present, the binding molecule is an antibody; and
   e) a capture molecule carries means for immobilization of the analyte, wherein the detection molecule and the capture molecule bind to different, non-overlapping epitopes on the analyte, and
   wherein the detection molecule is different from the binding molecule, wherein the analyte is different from the trapping molecule, wherein the detection molecule is only capable of forming a complex with the analyte when the analyte is not bound by the binding molecule, and wherein the detection molecule and capture molecule are each an antibody or a functionally active part of an antibody.

2. The kit or composition of claim 1, wherein the trapping molecule facilitates the essentially complete release of the analyte from the binding molecule.

3. The kit or composition of claim 1, wherein
K(trap)/K (binding molecule) is at least 3; and/or
Conc(trap)/Conc(binding molecule) is at least 3; and/or
(K(trap)/K(binding molecule)) x (Conc (trap)/Conc(binding molecule)) is at least 3; and/or
(K(trap)/K(binding molecule)) x (Conc(trap)/Conc (binding molecule)) x (MR (trap)/MR (binding molecule)) is at least 3;
wherein K(trap) is the affinity of the trapping molecule for the binding molecule and K(binding molecule) is affinity of the binding molecule for the analyte;
wherein Conc (trap) and Conc (binding molecule) are the molar concentrations of the trapping molecule and the binding molecule, respectively, wherein Conc (binding molecule) is in the range of from 1 to 5 µmol/l, and/or Conc(trap) is in the range of from 3*(1 to 5) µmol/l;
and wherein MR(trap) is the binding valence of the trapping molecule for binding to the binding molecule and MR(binding molecule) is binding valence of the binding molecule for binding to the analyte.

4. The kit or composition of claim 1, wherein:

the affinity of the detection molecule for binding to the analyte is at least $10^8$ (mol/1)-1; and/or the affinity of the trapping molecule for binding to the binding molecule is at least $5 \times 10^9$ $(mol/1)^{-1}$; and/or the molar concentration of the detection molecule is at most 5% of the molar concentration of the binding molecule in the sample.

* * * * *